United States Patent [19]

Schmerling et al.

[11] 4,100,359

[45] Jul. 11, 1978

[54] CARBONYLATION OF ALCOHOLS

[75] Inventors: Louis Schmerling, Riverside; Edwin H. Homeier, Maywood, both of Ill.

[73] Assignee: UOP Inc., Des Plaines, Ill.

[21] Appl. No.: 758,615

[22] Filed: Jan. 12, 1977

[51] Int. Cl.$^2$ ............... C07C 51/12; C07C 67/36
[52] U.S. Cl. .................................. 560/232; 260/532
[58] Field of Search ............... 260/488 K, 532; 560/232

[56] References Cited

U.S. PATENT DOCUMENTS 3,769,329  10/1973  Paulik et al. ............ 260/488 K

*Primary Examiner*—Vivian Garner
*Attorney, Agent, or Firm*—James R. Hoatson, Jr.; Raymond H. Nelson; William H. Page, II

[57] ABSTRACT

The carbonylation of alcohols in which an alcohol is treated with carbon monoxide may be improved by the use of a heterogeneous catalyst (namely, a chlorohodium phthalocyanine catalyst) promoted by a sulfonic acid or sulfonate group (either attached to the phthalocyanine compound or to an added organic compound) and an alkyl iodide.

9 Claims, No Drawings

CARBONYLATION OF ALCOHOLS

This invention relates to a process for the carbonylation of alcohols. More specifically, the invention is concerned with an improvement in the process for the carbonylation of alcohols whereby substantial yields of the desired carbonylated products, that is, carboxylic acids and esters thereof, can be obtained in a continuous flow process. The improvement in the process comprises use of catalysts which are insoluble in the reactants and products (i.e., are heterogeneous catalysts).

Certain carbonylated products such as esters and acids are important chemicals for use in the chemical industry. These products may be obtained from alcohols which are more readily available and which constitute a relatively inexpensive starting material. Therefore, it is of paramount importance that high yields of the desired products are obtained from the starting materials which are used in the process. Aliphatic esters are utilized in a variety of ways. For example, methyl acetate is used as a solvent, in extracts, perfumery, artificial leather, plastics, paints, varnishes and lacquers, etc. Likewise, ethyl propionate is also used as a solvent for cellulose ethers and esters, as a cutting agent, for pyroxylin, in fruit syrups, etc., while propyl butyrate is also used in solvent mixtures for cellulose ethers. In addition, the acids (such as acetic acid) are widely used as acids, as solvents, as reagents in the production of rubber, plastics, fibers, pharmaceuticals, dyes, insecticides, photographic chemicals as well as intermediates in the manufacture of anhydrides and esters. Propionic acid is used in the manufacture of propionates, some of these compounds being used as mold inhibitors in bread, as emulsion agents, as solutions for electroplating nickel or in perfume esters, artificial fruit flavors or pharmaceuticals.

It is therefore an object of this invention to provide a process for obtaining carbonylated products utilizing alcohols as a starting material.

A further object of this invention is found in a method for obtaining improved yields of desired carbonylated products in which an alcohol is treated with carbon monoxide in the presence of a metal phthalocyanine catalyst and an acid compound.

In one aspect an embodiment of this invention resides in a process for the carbonylation of a lower alkanol which comprises treating said alcohol with carbon monoxide in the presence of an activated metal phthalocyanine catalyst promoted by a sulfonyl group and an alkyl halide at carbonylation conditions, and recovering the resultant carbonylated product.

A specific embodiment of this invention resides in a process for the carbonylation of an alcohol which comprises treating methyl alcohol with carbon monoxide in the presence of chlororhodium phthalocyanine catalyst, a promoter compound comprising methyl iodide and toluenesulfonic acid at a temperature in the range of from about 100° to about 250° C. and a pressure in the range of from about 1 to about 200 atmospheres, and recovering the resultant methyl acetate and acetic acid.

Another specific embodiment of this invention resides in a process for the carbonylation of an alcohol which comprises treating methyl alcohol with carbon monoxide in the presence of a chlororhodium phthalocyaninetetrasulfonate catalyst and a promoter compound comprising methyl iodide at a temperature in the range of from about 100° to about 250° C. and a pressure in the range of from about 1 to about 200 atmospheres, and recovering the resultant methyl acetate and acetic acid.

Other objects and embodiments will be found in the following further detailed description of the present invention.

As hereinbefore set forth, the present invention relates to an improvement in a process for the carbonylation of alcohols whereby esters and acids may be obtained by the use of a heterogeneous catalyst. The carbonylation reaction is effected by treating an alcohol with carbon monoxide in the presence of certain catalysts and specifically metal phthalocyanine compounds in which the metal is selected from Group VIII transition metals, preferably the complexes of cobalt, rhodium or iridium, said catalyst being promoted by the presence of a sulfonyl group and an alkyl halide. The carbonylation reaction is effected under reaction conditions which include temperatures in the range of from about 100° to about 250° C. and preferably in a range of from about 150° to about 200° C. and pressures in a range of from about 1 to about 200 atmospheres. In the preferred embodiment of the invention the pressures under which the carbonylation reaction is effected will be afforded by the carbon monoxide which is present as one of the reactants. However, it is also contemplated that the carbon monoxide may afford only a partial pressure, the remainder of the operating pressure being provided for by the introduction of a substantially inert gas such as nitrogen into the reaction zone. Greater yields of the desired product are obtained in the presence of alkyl iodides in the reaction zone. The alkyl iodides which are added to the reaction zone may be aliphatic iodides such as methyl iodide and its homologs and aralkyl iodides such as benzyl iodides. They may also be formed in situ by the reaction of the alcohol and added hydroiodic acid.

By the term "sulfonyl group" as used in the present specification and appended claims is meant a sulfonic acid group or a sulfonate group. Suitable sulfonic acids include alkane- and cycloalkanesulfonic acids and arenesulfonic acids such as methanesulfonic acid, ethanesulfonic acid, benzenesulfonic acid, p-toluenesulfonic acid, naphthalenesulfonic acids, etc. Suitable sulfonates include salts of the sulfonic acids such as alkali metal, ammonium and alkaline earth salts such as sodium methanesulfonate, ammonium p-toluenesulfonate and magnesium 2-naphthalenesulfonate. Heavier metal salts, such as silver methanesulfonate, may also be employed, but not necessarily with equivalent results.

It is contemplated within the scope of this invention that the sulfonyl function may be attached to the phthalocyanine nucleus, for example, by utilizing a metal phthalocyaninesulfonate as the catalyst. Alternatively, it may be incorporated in an added compound such as toluenesulfonic acid.

The metal phthalocyanine compounds which are utilized as catalysts in the process of the present invention comprise, as hereinbefore set forth, a metal phthalocyanine in which the metal is a Group VIII transition metal and preferably cobalt, rhodium or iridium. In the manufacturing of the various metal phthalocyanine compounds, it is also contemplated that various anions may be bonded to the transition metal in the final catalytic composition of matter.

The anions which are present may be any negative valent ion which is present in the precursor of the metal phthalocyanine compound. For example, chlorine may be present in a rhodium phthalocyanine catalyst as the result of the precursor material which comprises rhodium trichloride, the end catalyst consisting of chlororhodium phthalocyanine. Other elements in the anions which may also be available in the manufacture of the catalyst include fluorine, bromine, iodine, phosphorus, sulfur, arsenic, nitrogen, etc. It is also contemplated within the scope of this invention that various metal complexing agents may be added to the catalyst in the reaction zone although not necessarily with equivalent results. Some examples of said metal complexing agents are arsines, phosphines, alkyl and aryl phosphites, etc. Suitable examples of the catalytic composition of matter which is used to effect the process of the present invention will comprise cobalt phthalocyanine, rhodium phthalocyanine, iridium phthalocyanine, chlororhodium phthalocyanine, chlorocobalt phthalocyanine, chloroiridium phthalocyanine, cobalt phthalocyaninecarboxylate, chlororhodium phthalocyaninecarboxylate, iridium phthalocyaninecarboxylate, cobalt phthalocyaninetetracarboxylate, chlororhodium phthalocyaninetetracarboxylate, iridium phthalocyaninetetracarboxylate, cobalt phthalocyaninetricarboxylate, chlororhodium phthalocyaninetricarboxylate, iridium phthalocyaninetricarboxylate, cobalt phthalocyaninedicarboxylate, chlororhodium phthalocyaninedicarboxylate, iridium phthalocyaninedicarboxylate, etc. In the event that the sulfonic acid or sulfonate function is to be included in the phthalocyanine compound, examples of these compounds would include cobalt phthalocyaninesulfonate, chlororhodium phthalocyaninesulfonate, iridium phthalocyaninesulfonate, cobalt phthalocyaninedisulfonate, chlororhodium phthalocyaninedisulfonate, iridium phthalocyaninedisulfonate, cobalt phthalocyaninetrisulfonate, chlororhodium phthalocyaninetrisulfonate, iridium phthalocyaninetrisulfonate, cobalt phthalocyaninetetrasulfonate, chlororhodium phthalocyaninetetrasulfonate, iridium phthalocyaninetetrasulfonate, etc. Alternatively, the phthalocyanine catalyst may contain no sulfonyl group on its nucleus, the group being present with the catalyst in the form of a compound such as p-toluenesulfonic acid.

It is also contemplated within the scope of this invention that compounds which act as promoters for the catalytic compositions of matter may also be present. Examples of these promoting compounds will include alkyl halides such as methyl iodide, ethyl iodide and propyl iodide, as well as less reactive alkyl halides such as methyl bromide, ethyl bromide, propyl bromide, methyl chloride, ethyl chloride, propyl chloride, etc., as well as a weak inorganic acid such as hydroiodic acid. Elemental iodine may also be used, if desired. The catalyst of the type hereinbefore set forth in greater detail will be present in the reaction mixture in a range of from about 0.1 to about 20% by weight based upon the alcohol which is to undergo carbonylation.

The process of this invention may be effected in any suitable manner and may comprise either a batch or continuous type of operation. For example, when a batch type operation is employed, a quantity of the alcohol and the catalyst is placed in an appropriate apparatus which is pressure-resistant in nature and may comprise an autoclave of the rocking or stirring type. In addition, the promoter compound or compounds is also placed in the reaction vessel which is then sealed and pressured with carbon monoxide and hydrogen in order to activate the catalyst. After activating the catalyst for a period of time which may range from about 0.5 up to about 4 hours or more in duration at temperatures ranging from about 50° to about 100° C. the gaseous products are discharged. Thereafter the vessel is again pressured to the desired operating pressure by the introduction of carbon monoxide and heated to a temperature in the range of from about 100° up to about 250° C. for a period of time which may range from about 0.5 up to about 20 hours or more in duration. At the end of the desired operating time, heating is discontinued and after the autoclave has returned to room temperature, the excess pressure is discharged. The autoclave is opened and the reaction mixture is recovered therefrom. After separation from the catalyst, the mixture is subjected to conventional means of separation and purification which may include washing, drying, fractional distillation, etc., whereby the desired carbonylated products comprising an ester and an acid are separated and recovered from the remainder of the reaction mixture.

It is also contemplated within the scope of this invention that the reaction may be effected in a continuous manner of operation. When such a type of operation is employed, a quantity of the alcohol is continuously charged to a reaction zone containing a metal phthalocyanine catalyst of the type hereinbefore set forth. Alternatively, the metal phthalocyanine catalyst may be supported on any inert support such as carbon, alumina, silica, zirconia, etc. The catalyst which is present in the reaction zone has previously been activated by treatment with hydrogen and carbon monoxide in a manner similar to that hereinbefore set forth. The remaining components of the reaction mixture including the promoter compound or compounds and the carbon monoxide are also continuously charged to this reaction zone which is maintained at the proper operating conditions of temperature and pressure. After passage through the reaction zone for a predetermined period of time, the reactor effluent is continuously withdrawn and subjected to conventional means of separation similar in nature to those previously discussed. The desired products comprising the ester and the acid are separated from any unreacted starting materials and recovered while the aforesaid unreacted starting materials may be recycled to the reaction zone to form a portion of the feed stock.

Examples of esters and acids which may be prepared according to the process of this invention will include acetate, ethyl propionate, propyl butyrate, butyl valerate, acetic acid, propionic acid, butyric acid, valeric acid, etc.

The following examples are given for purposes of illustrating the process of this invention in which improved yields of carbonylated products are obtained. However, it is to be understood that these examples are given merely for purposes of illustration and that the present process is not necessarily limited thereto.

EXAMPLE I

To illustrate the fact that the presence of promoters are required in order to obtain improved yields of desired products, an experiment was performed in which 100 grams (3.1 mole) of methanol along with 0.10 grams of chlororhodium phthalocyanine were placed in the glass liner of a rotating autoclave. The autoclave was then sealed and pressurized to an initial operating pressure of 90 atmospheres with carbon monoxide and heated to a temperature of 174° C. The autoclave and contents thereof were maintained at this temperature for a period of 4 hours, the maximum pressure during this reaction time reaching 190 atmospheres. At the end of the 4-hour period, heating was discontinued and the autoclave was allowed to return to room temperature, the final pressure at room temperature being 90 atmospheres. Upon reaching room temperature, the excess pressure was discharged and the autoclave was opened. Analysis of the product by means of gas-liquid chromatography disclosed that there had been little or no reaction, the major portion of the product being methyl alcohol.

The inside liner product of the above experiment which comprised 50 grams was placed in a second autoclave along with an additional amount of 50 grams of methyl alcohol. In addition, 2 grams of hydroiodic acid was added, the autoclave was sealed and pressured to 60 atmospheres with carbon monoxide. The autoclave was then heated to a temperature of 175° C. and maintained thereat for a period of 16 hours, the maximum pressure at this temperature reaching 143 atmospheres. At the end of the 16-hour period, heating was discontinued and the autoclave allowed to return to room temperature, the final pressure at room temperature being 53 atmospheres. The excess pressure was discharged and the autoclave was opened. Analysis of the inside liner product disclosed that there had been little or no reaction, the amount of acetic acid or methyl acetate formed being negligible.

EXAMPLE II

In this example 60 grams (1.9 mole) of methanol was placed in the glass liner of a rotating autoclave along with 1 gram of hydroiodic acid and 0.11 gram of chlororhodium phthalocyanine. The autoclave was sealed and pressured to 90 atmospheres by a combination of 70 atmospheres of carbon monoxide and 20 atmospheres of hydrogen. The autoclave was then heated to a temperature of 170° C. and maintained thereat for a period of 16 hours, the maximum pressure at this temperature reaching 168 atmospheres. At the end of the 16-hour period, heating was discontinued and the autoclave was allowed to return to room temperature, the final pressure at this temperature being 90 atmospheres. After discharge of the excess pressure and opening the autoclave, 27 grams of a blue liquid with a black suspended powder was recovered inside the liner. Analysis of this product disclosed that there had been little or no reaction.

When the above experiment was repeated using 60 atmospheres of carbon monoxide and 60 atmospheres of hydrogen, the result was identical in nature to that set forth in the above paragraph, that is, little or no reaction having occurred with a negligible amount of acetic acid and methyl acetate being recovered.

EXAMPLE III

The promoting effect of an added compound containing a sulfonyl group is illustrated in this example. In this experiment 51 grams of methanol, 0.10 grams of chlororhodium phthalocyanine, 0.15 grams of paratoluenesulfonic acid along with 1 gram of hydroiodic acid and 1 gram of methyl iodide were placed in the glass liner of a rotating autoclave. The autoclave was sealed and pressured with 80 atmospheres each of hydrogen and carbon monoxide. The autoclave was then heated to a temperature of 80° C. and maintained thereat for a period of 8 hours, the maximum pressure during this time reaching 181 atmospheres. At the end of the period, heating was discontinued and the autoclave allowed to return to room temperature. The excess pressure was discharged and the autoclave was then pressured with 90 atmospheres of carbon monoxide. After reaching the desired operating pressure, the autoclave was heated to a temperature of 175° C. and maintained thereat for a period of 8 hours, the maximum pressure at this temperature reaching 145 atmospheres. At the end of the 8-hour period, heating was discontinued and the autoclave was allowed to return to room temperature, the final pressure at room temperature being 73 atmospheres. This excess pressure was discharged and the autoclave was opened. The product in the liner was analyzed by gas chromatography and found to contain 10 mole % of a mixture of acetic acid and methyl acetate.

While it is to be noted that the mole % of carbonylated products was relatively small it is also noted that the amount of catalyst which was employed was also relatively small and that by utilizing a larger amount of catalyst it will be possible to obtain a greater amount or higher yield of the desired product.

EXAMPLE IV

The promoting effect of sulfonyl groups on the phthalocyanine nucleus is illustrated by this example. A mixture of 58 grams of methyl alcohol was charged to the glass liner of a rotating autoclave along with 0.014 mole of methyl iodide, 0.016 mole of hydroiodic acid and 0.37 grams of sodium chlororhodium phthalocyaninetetrasulfonate. The autoclave was sealed and 80 atmospheres of carbon monoxide and 80 atmospheres of hydrogen were charged thereto. The autoclave was then heated to a temperature of 80° C. and maintained thereat for a period of 16 hours, the maximum pressure during this time reaching 180 atmospheres. At the end of the 16-hour period, heating was discontinued and the autoclave was allowed to return to room temperature, the final pressure at room temperature being 148 atmospheres. The excess pressure was discharged and the autoclave was opened, 48 grams of a clear liquid with a green-black powder sediment being recovered therefrom. Gas chromatography showed that little or no reaction had occurred. Following this, 44 grams of the product which was recovered from the liner was then placed in a second autoclave which was sealed and pressured to 90 atmospheres with carbon monoxide. The autoclave was heated to a temperature of 200° C. and maintained thereat for a period of 16 hours, the maximum pressure during this time reaching 178 atmospheres. At the end of the 16-hour period, heating was discontinued and after the autoclave had returned to room temperature the final pressure was 65 atmospheres. The excess pressure was discharged and the autoclave was opened. Sixteen grams of the product in the liner which comprised a blue-green liquid over black powder was recovered. Analysis of this product by means of gas chromatography showed that there had been an 11 mole % conversion to methyl acetate and a 9 mole % conversion to acetic acid. The fact that there had been a conversion to the desired carbonylation products was due to the sulfonyl in the catalyst composition, namely, the sulfonate.

EXAMPLE V

In this example methyl alcohol was subjected to carbonylation in a manner similar to that set forth in the above examples, that is, by treating 41 grams of methanol and 2.64 grams of chlororhodium phthalocyaninemonosulfonate with 80 atmospheres of carbon monoxide and 80 atmospheres of hydrogen at a temperature of 80° C. for a period of 8 hours, 1 gram of methyl iodide being present to act as a promoter. After activating the catalyst in this manner, the excess pressure was discharged and the autoclave repressured with 90 atmospheres of carbon monoxide. The autoclave was then heated to a temperature of 175° C. for a period of 8 hours, the maximum pressure reaching 130 atmospheres. After discontinuing the heating and allowing the autoclave to return to room temperature, the final pressure at room temperature was 50 atmospheres. The autoclave was opened and the reaction product comprising 34 grams of a dark blue liquid plus some dark granules was recovered and subjected to gas chromatography. Analysis of this product disclosed that there had been a 25 mole % conversion to methyl acetate mixed with a lesser amount of acetic acid.

EXAMPLE VI

In a manner similar to that set forth in the above examples, 55.8 grams of methyl alcohol, 2.0 grams of cobalt phthalocyaninetetrasulfonate along with 3.2 grams of methyl iodide and 2.0 grams of toluenesulfonic acid were placed in the glass liner of a rocking autoclave. The autoclave was sealed and pressured by the introduction of 90 atmospheres of carbon monoxide. The autoclave was then heated to a temperature of 175° C. and maintained thereat for a period of 8 hours, the maximum pressure at this temperature reaching 148 atmospheres. At the end of the 8-hour period, heating was discontinued, the autoclave was allowed to return to room temperature and the excess pressure consisting of 78 atmospheres was discharged. The autoclave was opened and 12 grams of a dark blue liquid containing a suspension of very dark blue particles was recovered from the liner. Analysis of the product by means of gas chromatography showed that there had been a 5 mole % conversion to methyl acetate and a 2 mole % conversion to acetic acid.

We claim as our invention:

1. A process for the carbonylation of a lower alkanol compound which comprises treating said compound with carbon monoxide in the presence of a catalyst consisting essentially of; (1) a cobalt, rhodium, or iridium phthalocyanine compound free of sulfonic acid or sulfonate groups and promoters consisting essentially of both an alkyl halide and a sulfonic acid or sulfonate group donor compound selected from the group consisting of an alkanesulfonic acid, cycloalkanesulfonic acid, arenesulfonic acid, an alkali metal sulfonate, alkaline earth metal sulfonate and ammonium sulfonate, or (2) a cobalt, rhodium, or iridium phthalocyanine compound containing a sulfonic acid or sulfonate group and an alkyl halide promoter, at a temperature in the range of from about 100° to about 250° C. and a pressure within the range of from about 1 to 200 atmospheres, and recovering the resultant carbonylated product.

2. The process as set forth in claim 1 in which said alkythalide is methyl iodide.

3. The process as set forth in claim 1 in which said phthalocyanine compound is chlororhodium phthalocyanine containing a sulfonic acid or sulfonate group.

4. The process as set forth in claim 1 in which said arenesulfonic acid is a toluenesulfonic acid.

5. The process as set forth in claim 1 in which said arenesulfonic acid is benzenesulfonic acid.

6. The process as set forth in claim 1 in which said lower alkanol is methyl alcohol and said resultant carbonylated product is a mixture of methyl acetate and acetic acid.

7. The process as set forth in claim 1 in which said lower alkanol is ethyl alcohol and said resultant carbonylated product is a mixture of ethyl propionate and propionic acid.

8. The process as set forth in claim 1, in which said lower alkanol is propyl alcohol and said resultant carbonylated product is a mixture of propyl butyrate and butyric acid.

9. The process as set forth in claim 1 in which said metal phthalocyanine compound is rhodium (III) phthalocyaninetetrasulfonate.

* * * * *